(12) United States Patent
Jönsson et al.

(10) Patent No.: US 8,795,997 B2
(45) Date of Patent: *Aug. 5, 2014

(54) DETOXIFICATION WITH REDUCING AGENTS

(75) Inventors: Leif Jönsson, Umeå (SE); Björn Alriksson, Örnsköldsvik (SE); Adnan Cavka, Domsjö (SE)

(73) Assignee: Sekab E-Technology AB, Ornskoldsvik (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/517,284

(22) PCT Filed: Dec. 17, 2010

(86) PCT No.: PCT/EP2010/070127
§ 371 (c)(1),
(2), (4) Date: Sep. 25, 2012

(87) PCT Pub. No.: WO2011/080129
PCT Pub. Date: Jul. 7, 2011

(65) Prior Publication Data
US 2013/0011894 A1 Jan. 10, 2013

(30) Foreign Application Priority Data
Dec. 21, 2009 (EP) .................................... 09180193

(51) Int. Cl.
*C12P 7/10* (2006.01)

(52) U.S. Cl.
USPC ...................................................... 435/161

(58) Field of Classification Search
USPC ...................................................... 435/161
See application file for complete search history.

(56) References Cited

FOREIGN PATENT DOCUMENTS

WO WO 2008/076738 A2 6/2008
WO WO 2009/049067 4/2009

OTHER PUBLICATIONS

Kargi et al., Solid state fermentation of sweet sorghum to ethanol. Biotechnology and Bioengineering, vol. 27, (1985) pp. 34-40.*
Cantarella et al., Comparison of different detoxification methods for steam-exploded poplar wood as a substrate for the bioproduction of ethanol in SHF and SSF. Process Biochemistry, vol. 39 (2004) pp. 1533-1542.*
Larsson et al., Comparison of different methods for the detoxification of lignocellulose hydrolyzates of spruce. Applied Biochemistry and Biotechnology, vol. 77-79 (1999) pp. 91-103.*
Palmqvist et al., Fermentation of lignocellulosic hydrolysates I:Inhibition and detoxification. Bioresource Technology, vol. 74 (2000) pp. 17-24.*
Soudham et al., Reducing agents improve enzymatic hydrolysis of cellulosic substrates in the presence of pretreatment liquid. Journal of Biotechnology, vol. 155 (2011) pp. 244-250.*
Rotrekl et al., The role of cysteine residues in structure and enzyme activity of a maize B-glucosidase. European Journal of Biochemistry, vol. 266 (1999) pp. 1056-1065.*
Cavka et al., Effect of sulfur oxyanions on lignocellulose-derived fermentation inhibitors. Biotechnology and Bioengineering, vol. 108, No. 11 (Nov. 2011) pp. 2592-2599.*
Bhikhabhai et al., The disulphide bridges in a cellobiohydrolase and and endoglucanase from *Trichoderma reesei*. Biochemical Journal, vol. 222 (1984) pp. 729-736.*
Almeida, João R.M. et al., "Metabolic effects of furaldehydes and impacts on biotechnological processes", *Applied Microbiology and Biotechnology*, 2009, vol. 82, pp. 625-638.
Alriksson B. et al., "Improving the fermentability of enzymatic hydrolysates of lignocellulose through chemical in-situ detoxification with reducing agents", *Bioresource Technology*, vol. 102, Issue 2, Aug. 2010, pp. 1254-1263.
Bhikhabhai, R. et al., "The disulphide bridges in a cellobiohydrolase and an endoglucanase from *Trichoderma reesei*", *Biochemical Journal*, vol. 222, 1984, pp. 729-736.
International Preliminary Report on Patentability Corresponding to International Application No. PCT/EP2010/070127; Date of Mailing: May 14, 2012.
International Search Report Corresponding to International Application No. PCT/EP2010/070127; Date of Mailing: Jul. 8, 2011; 5 Pages.
Larsson, S. et al., "Comparison of Different Methods for the Detoxification of Lignocellulose Hydrolyzates of Spruce", *Applied Biochemistry and Biotechnology*, vol. 77-79, 1999, pp. 91-103.
Miller, E. et al., "Furfural Inhibits Growth by Limiting Sulfur Assimilation in Ethanologenic *Escherichia coli* Strain LY180", *Applied and Environmental Microbiology*, vol. 75, No. 19, Oct. 2009, pp. 6132-6141.
Olsson, L. et al., "Kinetics of Ethanol Production by Recombinant *Escherichia coli* KO11", *Biotechnology and Bioengineering*, vol. 45, No. 4, 1995, pp. 356-365.
Palmqvist, E. et al., "Fermentation of lignocellulosic hydrolysates. I: Inhibition and detoxification", *Bioresource Technology*, vol. 74, Issue 1, Aug. 2000, pp. 17-24.
Rotrekl, V. et al., "The role of cysteine residues in structure and enzyme activity of a maize β-glucosidase", *European Journal of Biochemistry*, vol. 266, 1999, pp. 1056-1065.
Soudham, V.P. et al., "Reducing agents improve enzymatic hydrolysis of cellulosic substrates in the presence of pretreatment liquid", *Journal of Biotechnology*, vol. 155, 2011, pp. 244-250.
U.S. Appl. No. 13/877,837, filed Apr. 4, 2013.
Chinese Application No. 201080064339.8; Office Action mailed Jul. 24, 2013.

* cited by examiner

*Primary Examiner* — Jon P Weber
*Assistant Examiner* — Kara Johnson
(74) *Attorney, Agent, or Firm* — Myers Bigel Sibley & Sajovec, P.A.

(57) ABSTRACT

The present invention provides a method for decreasing the fermentation inhibition in a process for producing a target chemical from a pretreated cellulosic material, the process comprising enzymatic hydrolysis of the pretreated cellulosic material and fermentation of hydrolysed material, wherein the fermentation inhibitory properties of the material subjected to fermentation is decreased by an addition of at least one reducing agent to the pretreated material or hydrolysed material. Moreover, the present invention provides the use of dithionite for decreasing the fermentation inhibitory properties of a material being subjected to simultaneous enzymatic hydrolysis and fermentation.

20 Claims, 9 Drawing Sheets

DETOXIFICATION WITH REDUCING AGENTS

RELATED APPLICATIONS

This application is a 35 U.S.C. §371 national phase application of PCT Application PCT/EP2010/070127, filed Dec. 17, 2010, which claims priority to EP 09180193.6, filed Dec. 21, 2009. The entire content of each of these applications is incorporated herein by reference.

TECHNICAL FIELD OF THE INVENTION

The present invention relates to a method for decreasing fermentation inhibitory effects of a slurry or hydrolysate during fermentation.

BACKGROUND ART

Biorefineries producing commodities from renewable resources offer an alternative to oil refineries based on dwindling supplies of petroleum and permit a move towards improved energy security. Lignocellulosic residues from forestry and agriculture are attractive as feedstocks, since they are abundant, relatively inexpensive, and are not used for food. Lignocellulose consists mainly of lignin and two classes of polysaccharides, cellulose and hemicellulose. The polysaccharides can be hydrolyzed to sugars and converted to various fermentation products, such as bioalcohols, in processes based on biocatalysts, such as the industrially important baker's yeast (*Saccharomyces cerevisiae*).

The hydrolysis of cellulose is typically preceded by a pretreatment, in which the hemicellulose is degraded and the cellulose is made increasingly accessible to cellulolytic enzymes. However, the pretreatment process typically generates fermentation inhibitors, such as phenolic compounds, aliphatic acids, and furan aldehydes, which have a negative effect on the efficiency of the fermentation process. Furthermore, it may be desirable to recirculate process water to achieve a cost-efficient and environmentally sound process. Such recycling of process may lead to accumulation of inhibitors that will contribute to the problems of poor fermentability.

SUMMARY OF THE INVENTION

Several methods are suggested to address inhibitor-related problems. These include choice of pretreatment conditions, design of fermentation procedure, strain selection, strain adaptation, mutation followed by selection and genetic engineering. However, manipulation of the pretreatment conditions to decrease formation of inhibitors or choosing the process design to avoid inhibitor problems can lead to decreased sugar yields, poor conversion of sugar, or poor ethanol yield and productivity. High sugar and ethanol yields and high productivity are essential for cost-efficient production of a high volume/low-value added product such as fuel ethanol Detoxification of hydrolysate, e.g. by addition of calcium hydroxide, is another suggested method. However, such alkali detoxification may result in extensive degradation of fermentable sugars. Furthermore, conventional detoxification methods generally requires extra process steps, such as steps in which the pH and/or temperature of the process stream need to be adjusted.

The inventors have realized that there is a need in the art for improved methods to overcome problems with fermentation inhibition in the manufacture of fermentation products from cellulosic material.

Therefore, it is an object of the present invention to provide a method for decreasing fermentation inhibition.

To meet this object, there is provided a method for decreasing the fermentation inhibition in a process for producing a target chemical from a pretreated cellulosic material, the process comprising enzymatic hydrolysis of the pretreated cellulosic material and fermentation of hydrolysed material, wherein the fermentation inhibitory properties of the material subjected to fermentation is decreased by an addition of at least one reducing agent to the pretreated material or hydrolysed material.

Moreover, there is provided the use of dithionite for decreasing the fermentation inhibitory properties of a material being subjected to simultaneous enzymatic hydrolysis and fermentation or a hydrolysate derived from enzymatic hydrolysis being subjected to fermentation.

DETAILED DESCRIPTION OF THE INVENTION

As a first aspect of the invention, there is provided a method for decreasing the fermentation inhibition in a process for producing a target chemical from a pretreated cellulosic material, the process comprising enzymatic hydrolysis of the pretreated cellulosic material and fermentation of hydrolysed material, wherein the fermentation inhibitory properties of the material subjected to fermentation is decreased by an addition of at least one reducing agent to the pretreated material or hydrolysed material.

"Fermentation" is a process known to the skilled person, and is usually performed by microorganisms.

"Fermentation inhibition" refers to a negative effect on a fermentation reaction, e.g. a decreasing of the rate of the fermentation reaction or the total amount of target product produced in the fermentation reaction. "Decreasing the fermentation inhibition" thus refers to decreasing such negative effect. Consequently, decreasing the fermentation inhibition may be detoxification or conditioning of a material subjected to fermentation, i.e. decreasing the effect of one or more properties of the material subjected to fermentation, which properties are inhibiting the fermenting organism's conversion of a substrate to the target chemical. For example, "decreasing the fermentation inhibition" may be increasing the saccharide consumption rate, such as the glucose consumption rate, increasing the total amount of target chemical produced during fermentation, increasing the target chemical yield on consumed saccharide during fermentation, i.e. increasing the number of target chemical molecules produced by each consumed saccharide molecule, or increasing the volumetric target chemical productivity, e.g. measured as (g target chemical$\times L^{-1} \times h^{-1}$)

A "cellulosic material" refers to any material comprising cellulose and/or hemicellulose. The cellulosic material may be lignocellulosic material, i.e. material comprising cellulose, lignin and possibly hemicellulose. The lignocellulosic material may for example be wood residues or forestry residues, such as wood chips, sawmill or paper mill discards, or agricultural residues, such as sugarcane bagass.

"Pretreated cellulosic material" refers to cellulosic material that has been pretreated in order to modify its properties such that the cellulose becomes more accessible during subsequent hydrolysis. The pretreatment may involve one or several pretreatment methods known to the skilled man. As an example, the pretreatment may be acid pretreatment or alkali pretreatment. Further, the pretreatment may be impregnation, which refers to impregnating of the cellulosic material with an impregnation fluid, followed by heating. The fluid may be an acid solution, such as a mineral acid solution. The impregnation may also be performed with a gas, such as a $SO_2$-gas or $CO_2$-gas, or with the combination of a gas with a liquid. The pretreatment may also comprise steaming. Steaming refers to a process used to drive air out from the cellulosic biomass to facilitate further hydrolysis of the cellulose. Steaming is a well-known method for pretreating e.g. lignocellulosic biomass. As another example, the pretreatment may involve steam explosion. Steam explosion is a process that combines steam, rapid pressure release and hydrolysis for rupturing cellulosic fibers.

A "target chemical from a pretreated cellulosic material" refers to any chemical that can be prepared from pretreated cellulosic material in a process comprising fermentation.

"Enzymatic hydrolysis" refers to a hydrolysis reaction catalysed by at least one enzyme. The at least one enzyme may be at least one saccharification enzyme, which refers to at least one enzyme that can convert or hydrolyse cellulosic material into fermentable saccharides, such as monosaccharides and/or disaccharides. Such saccharification enzymes may be glycosidases, which hydrolyse polysaccharides. Examples of glycosidases include cellulose-hydrolysing glycosidases, such as cellulases, endoglucanases, exoglucanases, cellobiohydrolases and β-glucosidases, hemicellulose hydrolysing glycosidases, such as xylanases, endoxylanases, exoxylanases, β-xylosidases, arabinoxylanases, mannanases, galactanases, pectinases and glucuronases, and starch hydrolysing glycosidases, such as amylases, α-amylases, β-amylases, glucoamylases, α-glucosidases and isoamylases, or any enzymes in the group of enzymes found in EC 3.2.1.x, such as EC 3.2.1.4, where EC is the Enzyme Commission number.

A "reducing agent" refers to a chemical agent capable of causing the reduction of another substance as it itself is oxidized, i.e. a chemical agent capable of donating an electron in an oxidation-reduction reaction.

The term "addition of at least one reducing agent to the pretreated material or hydrolysed material" thus refers to addition of at least one reducing agent to a cellulosic material that has already been subjected to pretreatment. Thus, according to the first aspect, the addition of the reducing agent occurs downstream of any pretreatment of cellulosic material in the process for producing a target chemical.

The present invention is based on the insight that the addition of a reducing agent to pretreated cellulosic material is an effective approach to overcome obstacles connected with bioconversion of cellulosic material to target chemicals. A dramatic improvement in fermentability can be achieved with a relatively small addition of reducing agent and further, the reducing agent is compatible with enzymes and fermenting organisms such as yeast, thus resulting in little influence on enzyme or yeast performance.

Furthermore, detoxification or conditioning of pretreated cellulosic material using a reducing agent according to the first aspect does not require introduction of genetically modified microorganisms in the industrial process. Further benefits of the method according to the first aspect of the invention include that the addition of the reducing agent can be carried out at a pH suitable for fermentation and at room or fermentation temperature, and results in improved fermentability without degradation of fermentable sugars. These benefits and the simplicity of the approach according to the first aspect offer a way to achieve more efficient manufacture of fermentation products, such as ethanol, from lignocellulose hydrolysates. Consequently, the method according to the first aspect of the invention provides for an efficient production of fuels, such as ethanol, and other chemicals from cellulosic materials.

In an embodiment of the first aspect, the enzymatic hydrolysis and fermentation are performed in two separate steps and the fermentation step is performed in a fermentor. A "fermentor" refers to any type of container that may be used for preparing a target chemical by means of fermentation. As an example, the cellulosic material may first be subjected to enzymatic hydrolysis to produce free sugars that in a separate process step are fermented into the target chemical. Thus, the process for producing a target chemical may be performed as a separate hydrolysis and fermentation (SHF) process. A SHF process offers the possibility to perform the enzymatic hydrolysis and fermentation at different process conditions, such as at different pH and temperature. As an example, if a SHF process is used, the at least one reducing agent may be added to the fermentor. Addition of the reducing agent to the fermentor is advantageous, since there is no need to perform any additional separate steps for addition of the reducing agent, which could contribute to higher process costs. Thus, addition of the reducing agent during fermentation permits full process flexibility, i.e. the general process design does not need to be adapted or amended for decreasing fermentation inhibition since the addition of a reducing agent is performed in the step of fermentation. The reducing agent may be added prior to or after a fermenting organism is added to the fermentor. Further, the reducing agent may be added concurrently with the fermenting organism.

In another embodiment of the first aspect, the enzymatic hydrolysis and fermentation are performed simultaneously in a fermentor. Thus, the process for producing a target chemical may be performed as a simultaneous saccharification and fermentation (SSF) process, in which hydrolysis of cellulosic material is achieved through addition of enzymes, such as cellulase, from external sources, or as a consolidated bioprocess (CBP), in which the biocatalyst that convert the monosaccharides also produces the enzymes that hydrolyze the cellulosic material. As an example, if the enzymatic hydrolysis and fermentation are performed simultaneously in a fermentor, as in an SSF process, the at least one reducing agent may be added to the fermentor. This is advantageous, since it permits full process flexibility and does not require any extra process steps during the production of the target chemical. Further, if the reducing agent is added to the fermentor, it may be added at any stage of the fermentation process, e.g. only if and when needed. As described above, the reducing agent may be added prior to or after enzymes and/or a fermenting organism are added to the fermentor. Further, the reducing agent may be added concurrently with the enzymes and/or the fermenting organism.

Consequently, if the reducing agent is added directly to a fermentor, the method according to the first aspect provides for a chemical in situ detoxification of the material subjected to fermentation.

However, if a SHF or SSF process is used, the reducing agent may also be added prior to the fermentor, such as during or after pretreatment of cellulosic material.

Further, it has also come to the inventors' insight that it may not be necessary to perform any adjustment of pH and/or temperature of the material subjected to fermentation to achieve the desired effect of a decrease in fermentation inhibitory properties. Therefore, in an embodiment of the first aspect of the invention, the at least one reducing agent is added at a temperature of 20-80° C., such as 20-75° C., such as 20-45° C., such as 28-38° C. Thus, the reducing agent may be added as the material subjected to fermentation has a temperature of 20-45° C., such as 28-38° C., which means that the reducing agent may be added at room temperature or at a temperature suitable for fermentation. Therefore, extra process steps for adjusting the temperature may not be required. Thermophilic enzymes may function at temperatures up to 80° C. and in such cases the reducing agent may be added in connection with the hydrolysis reaction, such as to the vessel in which hydrolysis is performed.

Preliminary results indicate that detoxification with reducing agents may be performed at various pH levels. The inventors have however noted that the detoxification with reducing agents appears to be more efficient at a pH above 3, such as above 4, than at a pH below 3, such as below 2.5. This means that the inventors believe that the detoxification is more efficient if it is performed after the pretreated material, which often has a pH of around 2, is neutralized.

Thus, in an embodiment of the first aspect, the least one reducing agent is added at a pH of 3-8, such as 3-6, such as 4-6, such as 5-6. This means that the reducing agent may be added at a pH that is suitable for hydrolysis and/or fermentation. For example, fermentation and SSF is often performed at a pH of about 5.5. Extra process steps for adjusting the pH may therefore not be required.

The inventors have found that it is preferable if the final concentration of the reducing agent during fermentation is within a certain interval. Therefore, in embodiments of the invention, the reducing agent is added to a final concentration during fermentation of 1-75 mM, such as 5-60 mM, such as 10-50 mM, such as 10-40 mM, such as 10-30 mM.

Further, in embodiments of the invention, the at least one reducing agent comprises sulphur. As an example, the at least one reducing agent may be selected from dithionite and sulphite. These reducing agents have shown to be suitable for decreasing the fermentation inhibition as shown in Examples 1-5 of the present disclosure. Sulphite ($SO_3^{2-}$) is used in several large-scale industrial processes. Dithionite ($S_2O_4^{2-}$) is an industrial chemical used in the pulp and paper industry for reductive bleaching and in the textile industry as a reducing agent in dyeing processes. Hence, both sulphite and dithionite may be available in large quantities. Further, it is to be understood the reducing agent may comprise sulphite and/or dithionite in salt form, i.e. complexed with different cations. Examples include $Na_2SO_3$, $NaHSO_3$, $KHSO_3$, and $Na_2S_2O_4$.

As an example, the reducing agent may be dithionite and the dithionite may be added in an amount such that the concentration of dithionite during fermentation is 1-30 mM, such as 5-25 mM, such as 7.5-20 mM. As a further example, the reducing agent may be sulphite and the sulphite may be added in an amount such that the concentration of sulphite during fermentation is 10-75 mM, such as 15-75 mM, such as 20-75 mM. Further, sulphite may be added in an amount such that the concentration of sulphite during fermentation is 10-60 mM, such as 15-50 mM, such as 20-40 mM. These concentrations of dithionite and sulphite, respectively, have shown to be suitable for decreasing fermentation inhibition, as shown in Examples 1-5 of the present disclosure. It may however be disadvantageous for the fermentation process to add more than 100 mM of sulphite. Thus, the amounts of dithionite or sulphite required to achieve a decrease in fermentation inhibitory properties are relatively low and the results from Examples 1-5 of the present disclosure show that such amounts of dithionite or sulphite permit production of high levels of ethanol using either SHF or SSF procedures. Further, it may be more advantageous to add dithionite compared sulphite, since dithionite results in a larger decrease in fermentation inhibition compared to sulphite when added to the same concentration, as seen in Examples 1-5 of the present disclosure. Consequently, the same fermentation inhibitory effect may be achieved by addition of a lower concentration of dithionite compared to sulphite. Addition of a lower concentration of dithionite compared to sulphite also means that the total salt concentration during fermentation is lower, which may be beneficial for the fermentation reaction.

Other compounds that may be used as reducing agents include thiosulphates ($S_2O_3^{2-}$), such as $Na_2S_2O_3.5H_2O$ and $Na_2S_2O_3$, alkali-decomposed sugars, ascorbic acid, cysteine, diethanolamine, triethanolamine, dithiothreitol (DTT) and reduced glutathione.

In embodiments of the invention, the target chemical is ethanol. Ethanol is a target chemical that is derivable from cellulosic biomass and which can be produced by means of fermentation. The target chemical may also be butanol or succinic acids, which are also derivable from cellulosic material. Other examples of target chemicals are other alcohols or acids, alkanes, alkenes, aromatics, aldehydes, ketones, biopolymers, proteins, peptides, amino acids, vitamins, antibiotics and other pharmaceuticals.

Further, the fermentation of hydrolysed material may be performed by a fermenting organism, which refers to an organism that is capable of fermenting saccharides into a target chemical. The fermenting organism may be at least one eukaryotic or prokaryotic microorganism, such as bacteria and/or yeast. Examples of bacteria and yeasts which are capable of fermenting saccharides into other chemical compounds are known to the skilled person. Yeasts from *Saccharomyces, Pichia* and *Candida* may be used as the fermenting organism. The fermenting organism may for example be wild type, mutant or recombinant *Saccharomyces cerevisiae*. Using *S. cerevisiae* for producing a target chemical by means of fermentation is advantageous since *S. cerevisiae* is well established with regard to industrial fermentation and provides for a high product yield.

In an embodiment of the first aspect of the invention, the material to which the reducing agent is added has a suspended solids content of at least 5% (w/w), such as at least 10% (w/w), such as at least 12% (w/w).

It has been found that the reducing agent may be added to a cellulosic material having relatively high solids content, such as the cellulosic material subjected to SSF or CBP. This enables detoxification or conditioning of pretreated slurry of cellulosic material without any solids separation step. Such in situ detoxification or conditioning provides for a high product yield and cost-efficient recovery of the target chemical, for example through distillation.

In an embodiment of the first aspect of the invention, the material to which the reducing agent is added has a sugar concentration of at least 45 g/l, such as at least 65 g/l, such as at least 85 g/l.

Consequently, the reducing agent may be added to a cellulosic material having a high sugar concentration, such as to the hydrolysed cellulosic material before or during the fermentation in a SHF process.

In the context of the present disclosure, "sugars" refers to fermentable saccharides, such as a fermentable monosaccharides and disaccharides.

In embodiments of the invention, the method according to the first aspect of the invention is further comprising measuring the fermentability of the fermentation of hydrolysed material; and if the measured fermentability is below a reference value, adding at least one reducing agent to the fermentation.

In the context of the present disclosure, the "fermentability" of a fermentation is any parameter that is proportional to the result of the fermentation process. As examples, the fermentability may be the sugar consumption rate, the amount of produced target chemical, the produced target chemical yield on consumed sugars and/or the volumetric target chemical productivity. The sugar consumption rate may be measured as the decrease of sugar concentration per hour, the amount of target chemical may be measured as g target chemical per liter, the produced target chemical yield on consumed sugars may be measured as the number of target chemical molecules produced by each consumed saccharide molecule by monitoring the decrease in saccharide concentration and the increase of target chemical concentration during fermentation, and the volumetric target chemical productivity may be measured as g target chemical per liter and hour. Further, the fermentability may be measured by measuring the total sugar concentration. If for example the fermenting organism becomes less effective in a SSF process, an increase of total sugar concentration may be measured. Thus, the fermentability may also be the inverse value of the total sugar concentration.

Thus, it has further come to the inventor's insight that, in the process for producing a target chemical from cellulosic biomass, an addition of at least one reducing agent to a fermentation process having a low fermentability may increase the fermentability of that process. Hence, this offers the possibility of "rescuing" a fermentation process that in some way does not function properly. As an example, the glucose consumption rate may be continuously monitored in a fermentation process and if the rate is below a satisfactory reference level, a reducing agent may be added in order to increase the glucose consumption rate. The reference value of the fermentability may for example be selected such that a fermentation process having a fermentability below the reference value, such as below a certain glucose consumption rate, leads to an unsatisfactory amount of target chemical, and a fermentation process with having a fermentability above the reference value, such as above a certain glucose consumption rate, leads to a desired amount of target chemical. Given the teachings of the present disclosure, the skilled person understands how to select a reference value for the fermentability.

It is shown in the Example referring to FIG. 8 below that the fermentation capacity in a fermentation that has been subjected to the inhibitors for a longer time may not completely recover even though the reducing agent is added. Without being bound by any scientific theory, the inventors believe that this may be due to that part of the yeast dies. Thus, in cases of insufficient fermentability in an ongoing fermentation or SSF, extra yeast may be added in addition the reducing agent. The extra yeast may be added before, concurrently or after the reducing agent. For example, the yeast and the reducing agent may be added within two hours, such as within one hour or 30 minutes.

In processes for producing a target chemical by means of fermentation, recirculation of process water generally leads to an accumulation of the inhibitory properties of the process water. However, since the addition of a reducing agent according to the first aspect of the invention decreases the fermentation inhibition, recirculation of process water may be performed without accumulating any inhibitory properties. Therefore, in embodiments of the first aspect, the method is further comprising recirculating process water obtained after the production of the target chemical to any step in the production of the target chemical.

Recirculation process water refers to reusing process water upstream in the process for producing a target chemical. As an example, part or all of the fermentation broth may be recirculated. Further, if the target chemical is extracted from the fermentation broth by means of distillation, part or all of the stillage (e.g. a filtrate of the stillage) may be recirculated. The recirculated process water may for example be used as a pretreatment fluid in a pretreatment of cellulosic material, as a hydrolysing liquid in a hydrolysis of cellulosic material or as a fermentation liquid in a fermentation of sugars.

Consequently, recirculation of process water decreases the need of introducing fresh water in the production of target chemicals from cellulosic biomass.

In a second aspect of the invention, there is provided the use of dithionite for decreasing the fermentation inhibitory properties of a material being subjected to simultaneous enzymatic hydrolysis and fermentation or a hydrolysate derived from a enzymatic hydrolysis being subjected to fermentation.

The terms and definitions used in the second aspect of the invention are as defined in connection with the first aspect above. Further, the embodiments of the first aspect apply mutatis mutandis to the second aspect.

Dithionite has been found to be advantageous for decreasing the fermentation inhibitory properties of a material in a simultaneous enzymatic hydrolysis and fermentation process, such as in a SSF or CBP. The dithionite may be used prior to or during the simultaneous enzymatic hydrolysis and fermentation process. The material may be a cellulosic material, such as a lignocellulosic material.

BRIEF DESCRIPTION OF THE DRAWINGS

FIG. 8 shows the ethanol production (g/L) after 24 h (black bars), 48 h (grey bars) and 72 h (white bars) of simultaneous saccharification and fermentation of spruce slurry of simultaneous saccharification and fermentation of spruce slurry. The data indicate: (A) 10 mM dithionite added 10 min prior to inoculum, (B) 10 mM sulphite added 10 min prior to inoculum, (C) 10 mM dithionite added at the time of inoculum, (D) 10 mM sulphite added at the time of inoculum, (E) 10 mM dithionite added 45 min after inoculum, (F) 10 mM sulphite added 45 min after inoculum, (G) 10 mM dithionite added 105 min after inoculum, (H) 10 mM sulphite added 105 min after inoculum, (I) 10 mM dithionite added 240 min after inoculum, (J) 10 mM sulphite added 240 min after inoculum, (K) 10 mM dithionite added 480 min after inoculum, (L) 10 mM sulphite added 480 min after inoculum, and (M) spruce slurry with no addition of reducing agent. Mean values based on two measurements are presented. Error bars indicate the standard deviations.

EXAMPLES

The following non-limiting examples will further illustrate the present invention.

Example 1

Detoxification of Hydrolysate in a Separate Hydrolysis and Fermentation (SHF) Process Materials and Methods Lignocellulose hydrolysates were produced from spruce wood and sugarcane bagass through thermochemical pretreatment and subsequent enzymatic hydrolysis.

For SHF experiments with sugarcane bagass, one kg (dry weight, DW) of dried sugarcane bagass was impregnated with 500 g of dilute sulfuric acid (4%) and kept in a plastic bag for 20 h. The impregnated sugarcane bagass was then loaded into a 30-liter reactor. The material was treated with steam at a temperature of 195° C. and a pressure of 14.1 bar during 15 min. The pretreated material, hereafter referred to as the sugarcane bagass slurry, was cooled and stored at 4° C. until further use.

The pretreatment of sugarcane bagass for SSF experiments was performed in the Swedish cellulosic ethanol pilot plant (operated by SEKAB E-Technology, Örnskoldsvik, Sweden). Sugarcane bagass was treated in a continuous mode in a 30-liter reactor at a temperature of 198-199° C. and with a residence time of 13-14 min. The feed rate was 24 kg (dry weight) per h and the bagass was impregnated with sulfur dioxide (0.5 kg/h). The pH after pretreatment was 2.7. The dry matter content was 19%. The pretreated material was cooled and stored at 4° C. until further use.

The pretreatment of spruce was also performed by SEKAB E-Technology in the Swedish cellulosic ethanol pilot plant. Unbarked wood chips were treated in a continuous mode with sulfur dioxide in a 30-liter reactor at a temperature of 203° C. and with a residence time of 5 min. One kg of sulfur dioxide per 40 kg of wood chips was used. The pH after pretreatment was 2.0-2.3. The dry matter content was 25-27%. The pretreated material was cooled and stored at 4° C. until further use. The pH of the bagass slurry was adjusted to 5.3 with a 5 M solution of sodium hydroxide. The slurry was then filtered and part of the liquid fraction was discarded to give the slurry a dry-matter content of 10%. Four 2-L shake flasks were filled with 750 g of slurry. The pH of the spruce slurry was adjusted to 5.3 with a 5 M solution of sodium hydroxide. Six 750-mL shake flasks were filled with 350 g of slurry. The dry-matter content was 16%.

Commercially available preparations of cellulase and cellobiase were added to the slurries. The cellulase preparation, which was from *Trichoderma reesei* ATCC 26921, had a stated activity of 700 endoglucanase units (EGU)/g (Sigma-Aldrich, Steinheim, Germany) and the loading was 319 EGU/g of solids (DW). The cellobiase preparation, Novozyme 188, had a stated activity of 250 cellobiase units (CBU)/g (Sigma-Aldrich) and the loading was 23 CBU/g of solids (DW). The enzyme dosages were based on the results of a set of small-scale experiments. After addition of enzymes, the slurries were incubated with shaking (Infors Ecotron, Infors AG, Bottmingen, Switzerland) at 50° C. and 70 rpm for 48 h.

After the hydrolysis, the slurries were filtered and the amounts of released glucose and mannose in the slurries were measured by high-performance liquid chromatography (HPLC). The pH of the liquid fractions, hereafter referred to as sugarcane bagass and spruce hydrolysate, was adjusted to pH 2.0 with a 12 M solution of hydrochloric acid to prevent microbial growth during storage. The sugarcane bagass hydrolysate was concentrated by evaporation (Rotavapor Büchi 001, Buchi Labortechnik AG, Flawil, Switzerland) to obtain a similar glucose concentration as in the spruce hydrolysate. The hydrolysates were stored at 4° C. until further use.

The pH of the sugarcane bagass and spruce hydrolysates were adjusted to 5.5 with a 5 M solution of sodium hydroxide. The conditioning of each hydrolysate was performed in eight 100-mL glass vessels equipped with magnetic stirrer bars. 26 mL hydrolysate was added to all vessels, and the vessels were placed on a magnetic stirrer plate (IKA-Werke, Staufen, Germany). Sodium dithionite (chemical grade; >87%, Merck, Darmstadt, Germany) was added to hydrolysates in the concentrations 5 and 10 mM. Additions of sodium sulphite to 5 and 10 mM were also performed. The additions were made at room temperature (23° C.) and the samples were kept for 10 min with stirring. The experiments were performed in duplicates.

The efficiency of the additions of the reducing agents was compared with alkali detoxification. Therefore, a hydrolysate sample was treated with ammonium hydroxide under conditions previously described (Alriksson et al. (2006), *Appl. Biochem. Biotechnol.* 129-132, 599-611.) The pH was adjusted to 9 and the hydrolysate was kept at 55° C. for 3 h with stirring.

Analyses of monosaccharides and furan aldehydes [furfural and 2-hydroxymethylfurfural (HMF)] were performed by using high-performance liquid chromatography (HPLC). A Shodex SH-1011 column (6 μm, 8×300 mm) (Showa Denko, Kawasaki, Japan) was used in a YoungLin YL9100 series system (YoungLin, Anyang, Korea) equipped with a YL9170 series refractive index (RI) detector for analysis of glucose, mannose, galactose, HMF, and furfural. Elution was performed with isocratic flow of a 0.01 M aqueous solution of $H_2SO_4$. The flow rate was 1.0 mL/min and the column temperature was set to 50° C. For analysis of xylose and arabinose, a Shodex SP-0810 column (7 μm, 8×300 mm) was used with the same HPLC system. The elution was performed using Milli-Q water at a flow rate of 1.0 mL/min and the column temperature was set to 80° C. YLClarity software (YoungLin, Anyang, Korea) was used for data analysis.

Determination of the total amount of phenolic compounds was performed using HPLC (MoRe Research, Örnskoldsvik, Sweden) according to a previously described method (Nilvebrant et al. (2001) *Appl. Biochem. Biotechnol.* 91-93, 35-49).

Ethanol measurements were performed by using an enzymatic kit (Ethanol UV-method, Boehringer Mannheim GmbH, Mannheim, Germany). Fermentation experiments were performed to evaluate the effectiveness of the additions and treatments. For comparison, untreated hydrolysates were included in the fermentation experiments as well as reference fermentations of sugar-based medium with an amount of fermentable sugars (i.e. glucose and mannose) corresponding to that in the hydrolysate samples. The fermentations were carried out using baker's yeast (*Saccharomyces cerevisiae*) (Jastbolaget AB, Rotebro, Sweden). The yeast inoculum was prepared in 750-mL cotton-plugged shake flasks with 300 mL YEPD medium (2% yeast extract, 1% peptone, 2% D-glucose). The flasks were inoculated and incubated with agitation at 30° C. for approximately 12 h. The cells were harvested in the late exponential growth phase by centrifugation (Hermla Z206A, Hermle Labortechnik GmbH, Wehingen, Germany) at 1,500 g for 5 min. The cells were resuspended in an appropriate amount of sterile water to achieve an inoculum consisting of 2.0 g/L (cell dry weight) in all fermentation vessels. The fermentation was carried out in 14 25-mL glass flasks equipped with magnets for stirring and sealed with rubber plugs pierced with cannulas for letting out carbon dioxide. The hydrolysate samples (23.75 mL), or alternatively the sugar solution for reference fermentations, were added to the fermentation flasks along with 0.5 mL of a nutrient solution (150 g/L yeast extract, 75 g/L $(NH_4)_2HPO_4$, 3.75 g/L $MgSO_4.7H_2O$, 238.2 g/L $NaH_2PO_4.H_2O$), and 0.75 mL of yeast inoculum. The flasks were incubated at 30° C. in a water bath with magnetic stirring (IKA-Werke). Samples for measurement of sugars and ethanol were withdrawn during the fermentation. The glucose levels during the fermentation were estimated by using a glucometer (Glucometer Elite XL, Bayer AG, Leverkusen, Germany).

Results

The preparation of spruce and sugarcane bagass hydrolysates for SHF experiments resulted in hydrolysates with over 80 g/L glucose and more than 100 g/L of monosaccharides (Tables 1 and 2). Glucose was the predominant fermentable sugar in both hydrolysates, but the spruce hydrolysate contained, as expected, large amounts of mannose (Table 1). The total concentrations of phenolic compounds, as estimated by HPLC, were relatively similar. Both hydrolysates contained about four g/L furan aldehydes and about three times as much HMF as furfural. The contents of aliphatic acids were slightly higher in the spruce hydrolysate than in the sugarcane bagasse hydrolysate. In both cases, acetic acid was most common among the aliphatic acids.

The concentrations of monosaccharides were not affected by the additions of dithionite or sulphite (Tables 1 and 2). However, the alkali detoxification, i.e. the addition of $NH_4OH$, resulted in lower sugar concentrations compared to addition of dithionite or sulphite. For example, the glucose concentration of the spruce hydrolysate after alkali detoxification was only about 70 g/L, whereas addition of dithionite or sulphite led to glucose concentrations above 80 g/L. Alkali detoxification also led to smaller amounts of xylose, galactose and mannose in the spruce hydrolysate compared to when dithionite or sulphite were used. Further, alkali detoxification led to smaller amounts of xylose and galactose in the sugarcane bagasse hydrolysate compared to when dithionite or sulphite were added (Tables 1 and 2). Consequently, addition of dithionite and sulphite resulted in higher sugar concentrations compared to alkali detoxification.

TABLE 1

Concentrations (g/L) of monosaccharides and inhibitors in the spruce hydrolysate used for experiments with separate hydrolysis and fermentation.

|  | Glucose | Xylose | Galact | Mannose | Arabin. | Phen. | Furfural | HMF | Acetic acid | Levulinic acid | Formic acid |
|---|---|---|---|---|---|---|---|---|---|---|---|
| Untreat. hydro. | 82.9 ± 4.7 | 9.1 ± 0.1 | 3.7 ± 0.1 | 26.4 ± 0.5 | 2.8 ± 0.1 | 0.38 ± 0.01 | 1.2 ± 0.1 | 3.2 ± 0.1 | 4.7 ± 0.3 | 0.2 ± 0.1 | 0.6 ± 0.1 |
| Dithionite (5 mM) | 83.3 ± 1.2 | 9.2 ± 0.1 | 3.9 ± 0.4 | 26.5 ± 0.1 | 3.0 ± 0.1 | 0.42 ± 0.01 | 0.9 ± 0.1 | 3.4 ± 0.1 | 5.2 ± 0.1 | 0.2 ± 0.1 | 0.7 ± 0.1 |
| Dithionite (10 mM) | 82.4 ± 2.9 | 9.2 ± 0.1 | 3.8 ± 0.3 | 26.4 ± 0.7 | 2.9 ± 0.2 | 0.44 ± 0.05 | 1.0 ± 0.1 | 3.3 ± 0.2 | 5.0 ± 0.4 | 0.2 ± 0.1 | 0.7 ± 0.1 |
| Sulphite (5 mM) | 81.1 ± 0.8 | 9.1 ± 0.1 | 3.9 ± 0.1 | 26.2 ± 0.3 | 3.0 ± 0.2 | 0.43 ± 0.02 | 1.0 ± 0.1 | 3.4 ± 0.1 | 4.7 ± 0.2 | 0.2 ± 0.1 | 0.6 ± 0.1 |
| Sulphite (10 mM) | 82.4 ± 0.2 | 9.2 ± 0.1 | 3.8 ± 0.4 | 26.4 ± 0.7 | 2.9 ± 0.1 | 0.39 ± 0.03 | 1.0 ± 0.1 | 3.4 ± 0.1 | 5.1 ± 0.3 | 0.2 ± 0.1 | 0.7 ± 0.1 |
| $NH_4OH$-detox. | 72.4 ± 5.5 | 8.2 ± 0.1 | 3.3 ± 0.1 | 23.3 ± 0.7 | 2.8 ± 0.2 | 0.39 ± 0.03 | 0.7 ± 0.1 | 1.7 ± 0.1 | 4.7 ± 0.2 | 0.2 ± 0.1 | 0.7 ± 0.1 |

Abbreviations used:
Galact = galactose;
Arabin = arabinose;
Phen = phenolic compounds;
HMF = 2-hydroxymethylfurfural;
Untreat. hydro = untreated hydrolysate;
$NH_4OH$-detox. = ammonium hydroxide detoxification.

TABLE 2

Concentrations (g/L) of monosaccharides and inhibitors in the sugarcane bagass hydrolysate used for experiments with separate hydrolysis and fermentation.

|  | Glucose | Xylose | Galact | Mannose | Arabin. | Phen. | Furfural | HMF | Acetic acid | Levulinic acid | Formic acid |
|---|---|---|---|---|---|---|---|---|---|---|---|
| Untreat. hydro. | 86.3 ± 0.9 | 14.1 ± 0.1 | 9.8 ± 0.1 | 0.5 ± 0.1 | 0.2 ± 0.1 | 0.58 ± 0.03 | 1.0 ± 0.1 | 3.0 ± 0.2 | 3.2 ± 0.1 | 0.2 ± 0.1 | 0.6 ± 0.1 |
| Dithionite (5 mM) | 85.3 ± 0.6 | 14.5 ± 0.3 | 9.4 ± 0.1 | 0.4 ± 0.1 | 0.2 ± 0.1 | 0.62 ± 0.01 | 0.9 ± 0.1 | 3.0 ± 0.1 | 3.4 ± 0.1 | 0.3 ± 0.1 | 0.7 ± 0.1 |
| Dithionite (10 mM) | 85.8 ± 0.4 | 14.3 ± 0.7 | 9.5 ± 0.4 | 0.3 ± 0.1 | 0.3 ± 0.1 | 0.54 ± 0.06 | 0.9 ± 0.1 | 3.0 ± 0.1 | 3.6 ± 0.3 | 0.3 ± 0.1 | 0.8 ± 0.1 |
| Sulphite (5 mM) | 85.0 ± 0.2 | 14.1 ± 0.3 | 9.6 ± 0.7 | 0.3 ± 0.1 | 0.2 ± 0.1 | 0.56 ± 0.04 | 1.0 ± 0.1 | 2.9 ± 0.1 | 3.1 ± 0.4 | 0.3 ± 0.1 | 0.7 ± 0.1 |
| Sulphite (10 mM) | 85.6 ± 0.2 | 14.3 ± 0.1 | 9.6 ± 0.1 | 0.4 ± 0.1 | 0.2 ± 0.1 | 0.63 ± 0.01 | 1.0 ± 0.1 | 3.0 ± 0.1 | 3.3 ± 0.1 | 0.3 ± 0.1 | 0.7 ± 0.1 |
| $NH_4OH$-detox. | 85.8 ± 0.4 | 12.6 ± 0.2 | 8.6 ± 0.1 | 0.3 ± 0.1 | 0.2 ± 0.1 | 0.60 ± 0.01 | 0.6 ± 0.1 | 1.6 ± 0.1 | 3.2 ± 0.1 | 0.2 ± 0.1 | 0.7 ± 0.1 |

Abbreviations used:
Galact = galactose;
Arabin = arabinose;
Phen = phenolic compounds;
HMF = 2-hydroxymethylfurfural;
Untreat. hydro = untreated hydrolysate;
$NH_4OH$-detox. = ammonium hydroxide detoxification.

Figure 1:
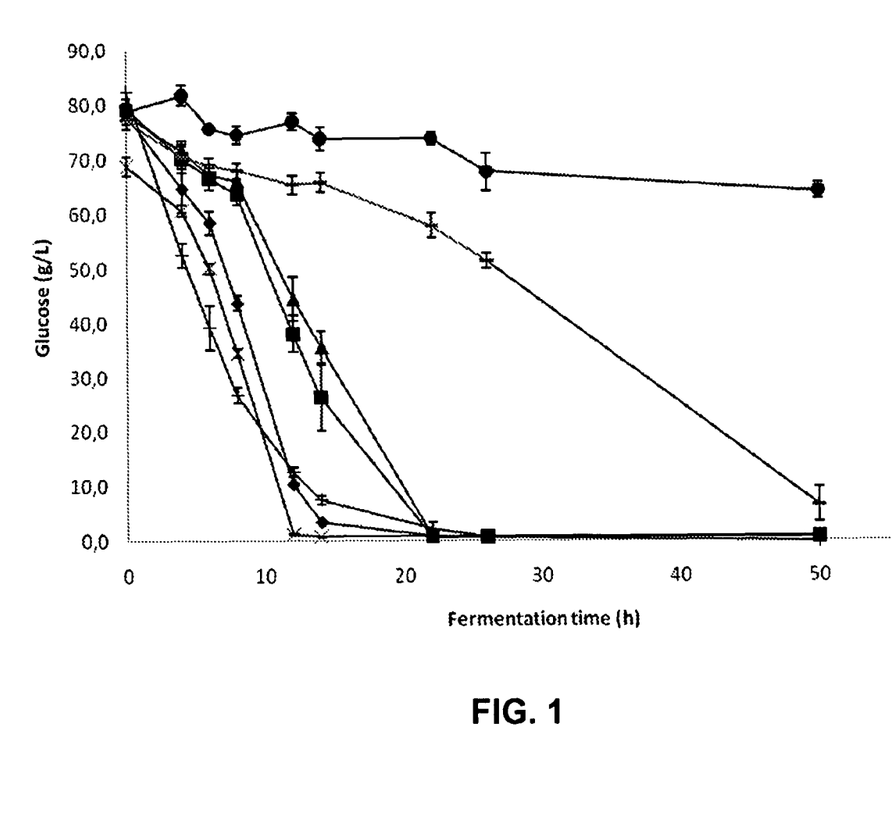
FIG. 1 shows the glucose consumption in the experiment with separate hydrolysis and fermentation of a spruce hydrolysate. Every point in the graph is calculated as the mean value of two fermentations. The error bars indicate the standard deviations. The data indicate: ■: dithionite addition (5 mM), ♦: dithionite addition (10 mM), -: sulphite addition (5 mM), ▲: sulphite addition (10.0 mM), ●: untreated hydrolysate, x: NH$_4$OH treatment and +: reference fermentation.
Figure 2:
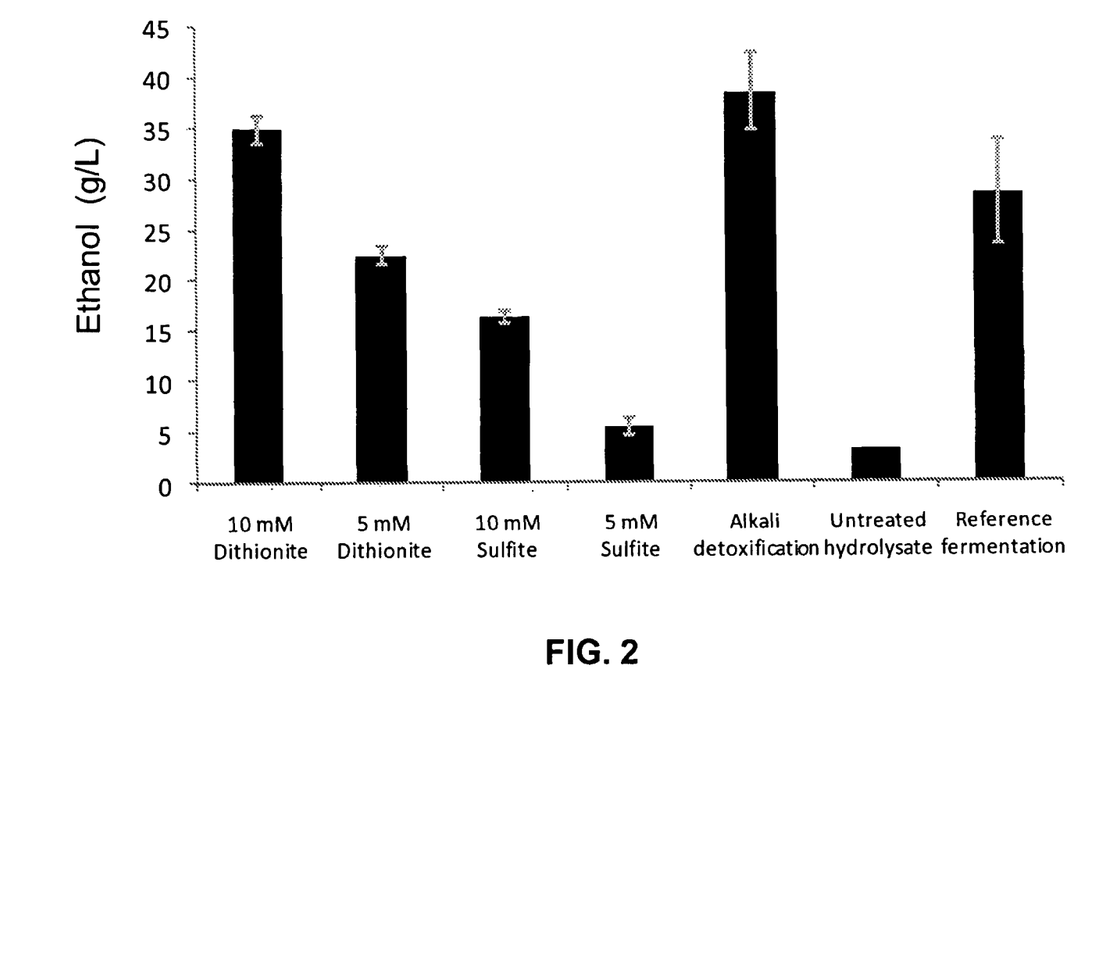
FIG. 2 shows the ethanol production (g/L) after 14 h fermentation of the spruce hydrolysate (separate hydrolysis and fermentation experiment). Every bar is calculated as the mean value of two fermentations. The error bars indicate the standard deviations.

Only a very small fraction of the glucose was consumed in untreated spruce hydrolysate even after 50 h of fermentation, which shows that the spruce hydrolysate was very inhibitory (FIG. 1). The glucose consumption rates (FIG. 1) and the amounts of ethanol produced (FIG. 2) in spruce hydrolysate with 10 mM dithionite were comparable to those of the reference fermentation. The samples with 5 mM dithionite or 10 mM sulphite showed a substantial improvement compared to untreated hydrolysate (FIGS. 1 and 2).

Figure 3:
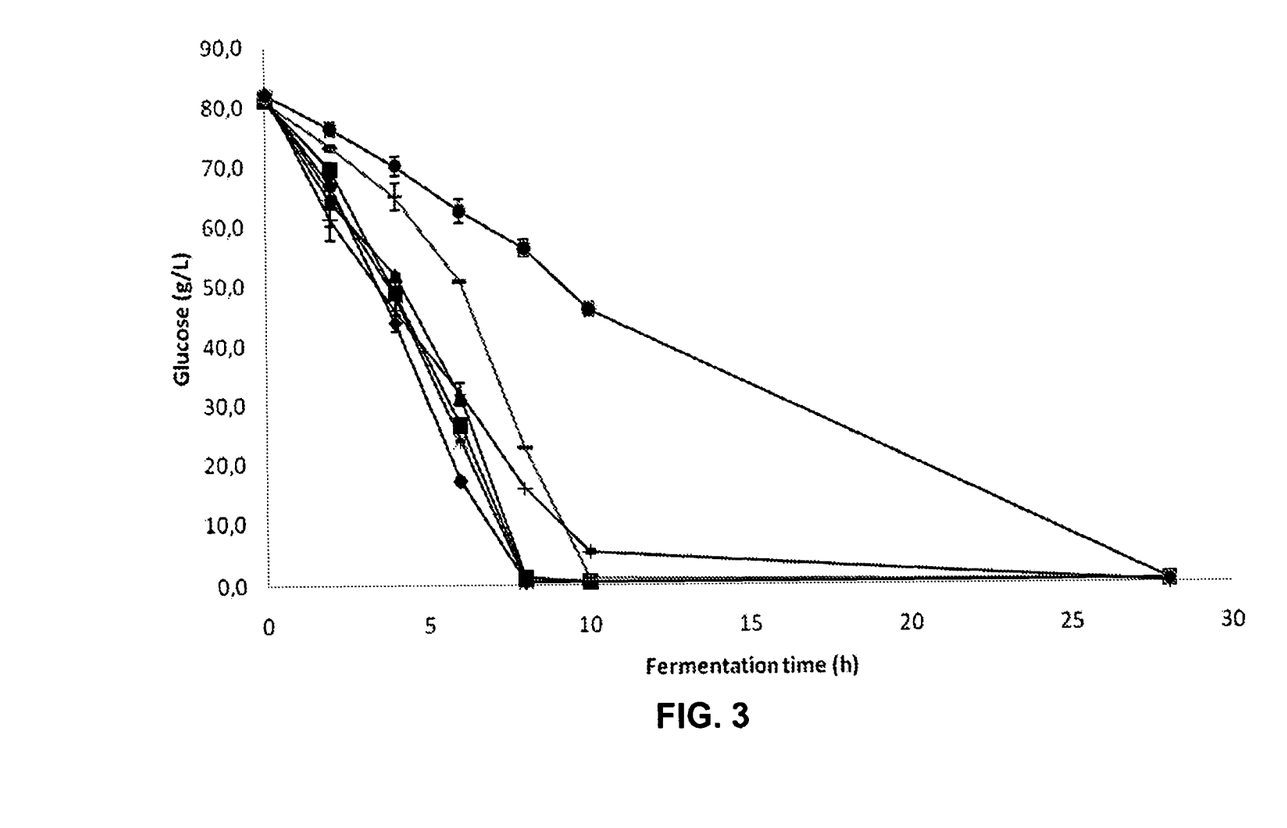
FIG. 3 shows the glucose consumption in the experiment with separate hydrolysis and fermentation of the sugarcane bagass hydrolysate. Every point in the graph is calculated as the mean value of two fermentations. The error bars indicate the standard deviations. The data indicate: ■: dithionite treatment (5 mM), ♦: dithionite treatment (10.0 mM), -: sulphite (5 mM). ▲: sulphite treatment (10.0 mM), ●: untreated hydrolysate, x: NH$_4$OH treatment and +: reference fermentation.

The sugarcane bagass hydrolysate was not as inhibitory as the spruce hydrolysate, since there was a steady consumption of glucose, which was depleted in the sample taken after 28 h of fermentation (FIG. 3). The differences between the effects of the various treatments were therefore less pronounced in the sugarcane bagass hydrolysates, but they follow the same pattern as observed in the spruce hydrolysate.

Figure 4:
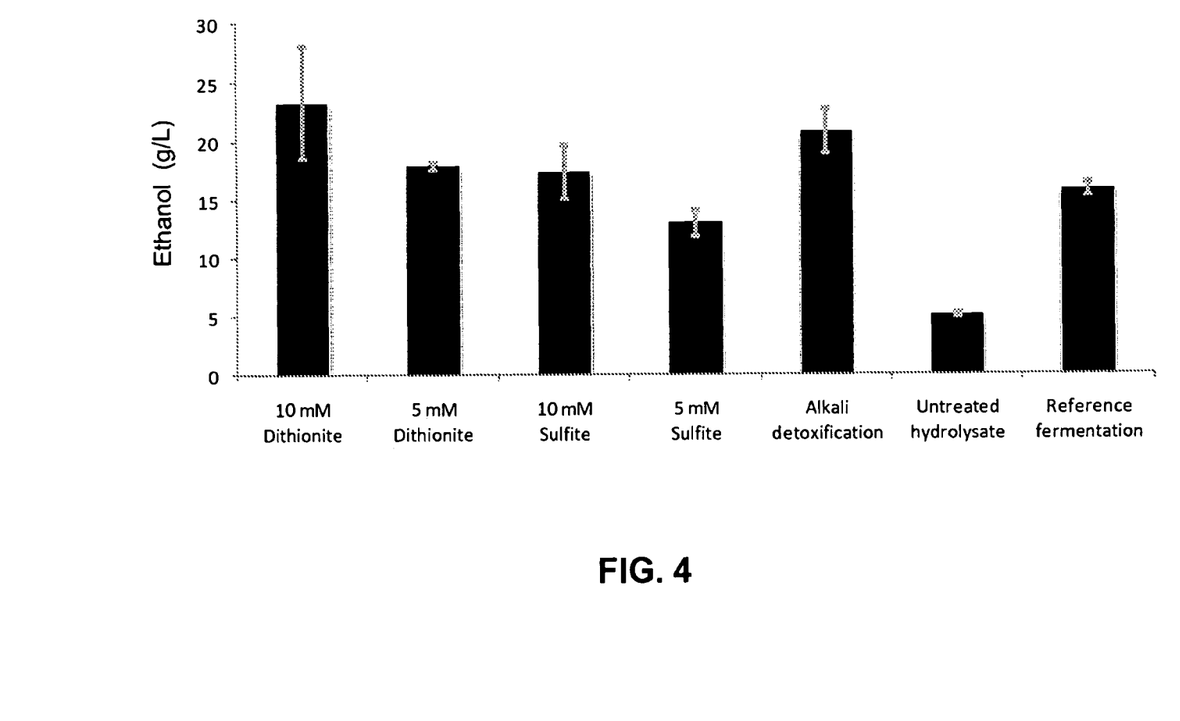
FIG. 4 shows the ethanol production (g/L) after 6 h fermentation of the sugarcane bagass hydrolysate (separate hydrolysis and fermentation). Every bar is calculated as the mean value of two fermentations. The error bars indicate the standard deviations.

Addition of dithionite or sulphite also resulted in high ethanol production from sugarcane bagass hydrolysate, as seen in FIG. 4. Addition of 10 mM dithionite and resulted in a higher ethanol concentration compared to addition of 5 mM dithionite or 10 mM sulphite.

The ethanol yields on consumed sugars (Table 3) were improved by addition of dithionite or sulphite. For dithionite addition, the ethanol yields were even higher than in the reference fermentations (Table 3). The ethanol yield was comparable to those found using the alkali detoxification.

TABLE 3

Ethanol yield and productivity in experiments with separate hydrolysis and fermentation. The table shows the values obtained after 14 h (spruce hydrolysate) and 6 h (sugarcane bagass hydrolysate) fermentation.

|  | Yield | | Productivity | | Balanced ethanol yield | |
|---|---|---|---|---|---|---|
|  | Spruce hydro. | Bagass hydro. | Spruce hydro. | Bagass hydro. | Spruce Hydro. | Bagass Hydro. |
| Untreated hydro. | 0.21 | 0.21 | 0.2 | 0.9 | 0.03 | 0.06 |
| Dithionite (10 mM) | 0.37 | 0.34 | 2.5 | 3.9 | 0.34 | 0.28 |
| Sulphite (10 mM) | 0.29 | 0.32 | 1.2 | 2.9 | 0.16 | 0.21 |
| $NH_4OH$ detox. | 0.43 | 0.34 | 2.8 | 3.5 | 0.37 | 0.25 |
| Ref. ferment. | 0.33 | 0.29 | 2.0 | 2.6 | 0.28 | 0.19 |

Abbreviations used:
spruce hydro. = spruce hydrolysate;
sugarcane bagass hydro. = sugarcane bagass hydrolysate;
untreated hydro. = untreated hydrolysate;
$NH_4OH$ detox. = $NH_4OH$ detoxification;
Ref. Ferment = reference fermentation.
Yield is expressed as g EtOH/g consumed glucose & mannose.
Productivity is expressed as (g EtOH×$L^{-1}$×$h^{-1}$).
Balanced ethanol yield is expressed as g EtOH/Σglucose & mannose prior to detoxification.

Further, the volumetric ethanol productivities for samples treated by addition of dithionite or by ammonium hydroxide detoxification rose significantly and were higher than the corresponding values for the reference fermentation (Table 3).

Consequently, addition of dithionite or sulphite resulted in ethanol yields that were in line with or higher than the yield of the reference fermentation. Moreover, dithionite addition also resulted in an ethanol productivity that was higher than the reference fermentation.

Thus, Example 1 shows that the addition of reducing agents radically improved the femientability of inhibitory lignocellulose hydrolysates in the SHF process without the need for a separate detoxification step.

Example 2

Detoxification of Hydrolysate in a Simultaneous Saccharification and Fermentation (SSF) Process Materials and Methods Addition of sodium dithionite and sodium sulphite was tested in an SSF process. Spruce was pretreated as described in Example 1 above. The spruce slurry was adjusted to pH 5.4 with a 5 M solution of sodium hydroxide. Ten 250-mL shake flasks equipped with magnetic stirrer bars were filled with 100 g of spruce slurry. Sodium dithionite or sodium sulphite was added to the slurries to final concentrations of 7.5 and 10 mM. The additions were performed at room temperature (23° C.) for 10 min with stirring. Duplicate experiments were made. Cellulase and cellobiase preparations were prepared and added to the slurry using the enzyme activity loadings as described in Example 1 above. Further, the yeast inoculum was prepared according to Example 1 above. Inoculums were added to give a start concentration of 2.0 g/L (cell dry weight) in every flask. No source of extra nutrients was added. For comparison, two flasks with spruce slurry to which no reducing agents had been added were included in the experiment. The flasks were incubated at 35° C. for 69 h in a water bath with magnetic stirring. The flasks were sealed with Parafilm (Pechiney Plastic Packaging Company, Chicago, Ill., USA) to prevent evaporation of ethanol. Samples were withdrawn for analysis of ethanol according to Example1 above.

Results

Figure 5:
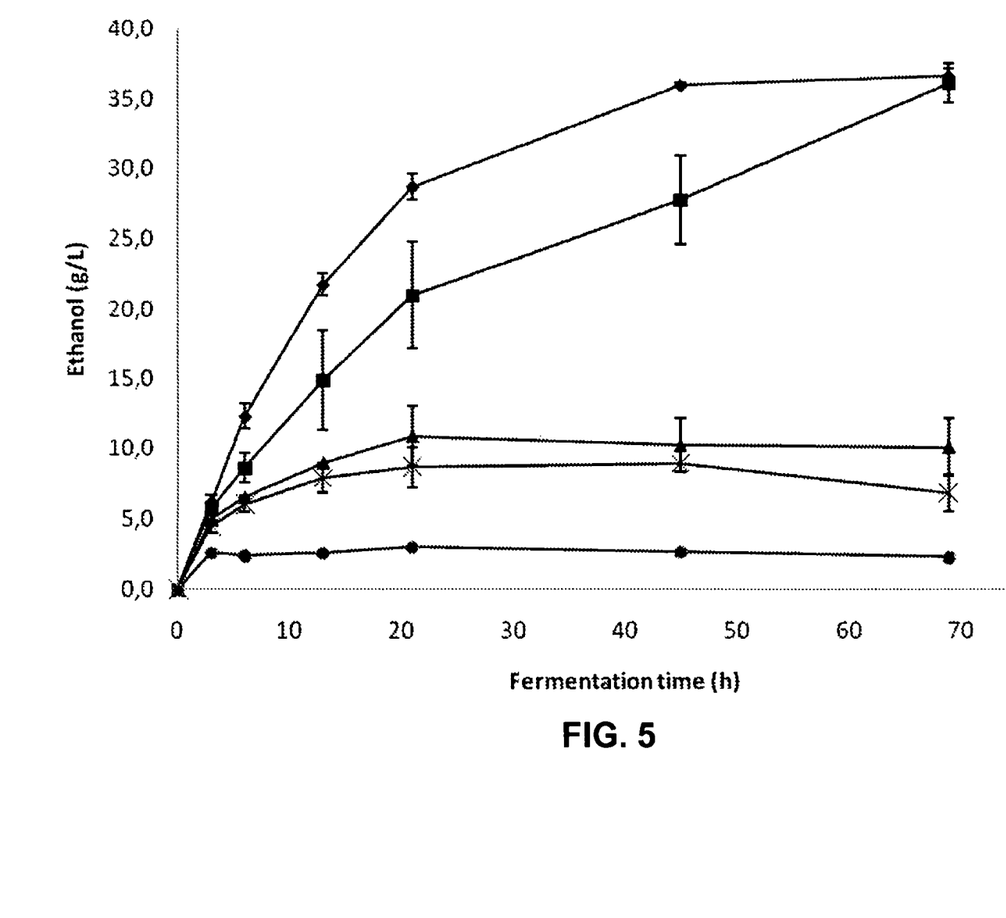
FIG. 5 shows the ethanol production during simultaneous saccharification and fermentation of spruce slurry. Every point in the graph was calculated as the mean value of two fermentations. The error bars indicate the standard deviations. The data indicate: ■: dithionite treatment (7.5 mM), ♦: dithionite treatment (10 mM), x: sulphite treatment (7.5 mM), ▲: sulphite treatment (10 mM) and ●: untreated slurry.

The result of the SSF experiment with spruce slurry is shown in FIG. 5. FIG. 5 clearly shows that addition of dithionite and sulphite led to higher ethanol production compared to the untreated hydrolysate. The ethanol formation in the samples with 10 mM dithionite leveled off after about 45 h. The samples with 7.5 mM dithionite reached the same high levels of ethanol, but ethanol formation was slightly slower. Ethanol formation in the samples to which sulphite was added leveled off after 20 h and resulted in a lower ethanol production compared to the samples to which dithionite was added (FIG. 5).

Thus, Example 2 shows that the addition of reducing agents radically improved the fermentability of inhibitory lignocellulose hydrolysates also in the SSF process without the need for a separate detoxification step. Dithionite and sulphite were chosen for the SSF process considering their utilization in large-scale industrial processes.

Example 3

Detoxification of Spruce Slurry in a Simultaneous Saccharification and Fermentation (SSF) Process: Ethanol Yield as a Function of Dithionite and Sulphite Concentrations Materials and Methods A spruce slurry was prepared according to Examples 1 and 2 above. Different flasks were filled with 100 g each of the spruce slurry and were subjected to a SSF process according to Example 2 above, but with different amounts of dithionite and sulphite added. The produced ethanol was monitored during the fermentation.

Results

Sodium dithionite was added such that the final concentration during fermentation was between 2.5-30 mM. Further, sodium sulphate was added such that the final concentration during fermentation was between 2.5-30 mM. The produced ethanol as a function of time is plotted in FIG. 6 and FIG. 7.

Figure 6:
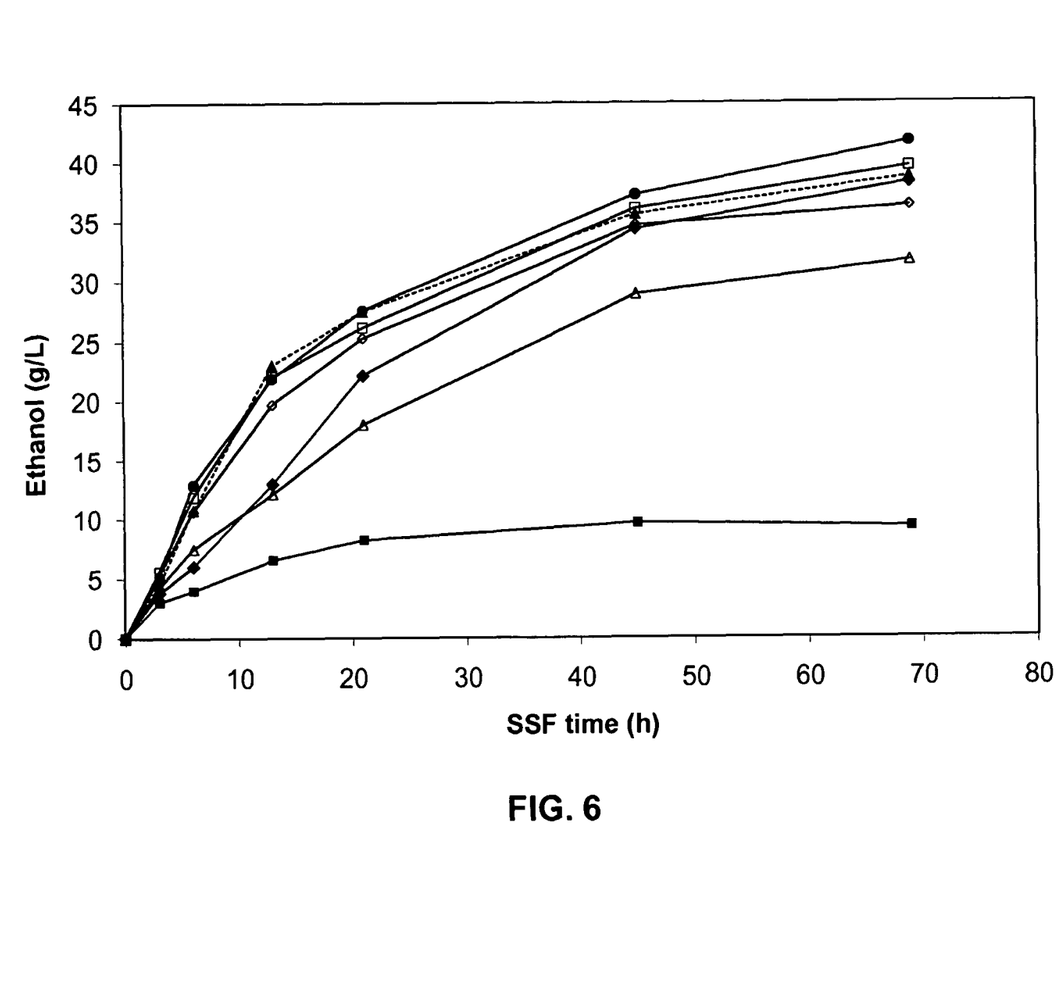
FIG. 6 shows the ethanol production during simultaneous saccharification and fermentation of spruce slurry with addition of different concentrations of dithionite. The data represent: ■: solid line: dithionite treatment (2.5 mM); ♦, solid line: dithionite treatment (5 mM); ▲, dashed line: dithionite treatment (7.5 mM); ●: solid line: dithionite treatment (10 mM); □, solid line: dithionite treatment (15 mM); ◊, solid line: dithionite treatment (20 mM); Δ, solid line: dithionite treatment (30 mM).

It was seen that treatment with 7.5 mM, 10 mM and 15 mM sodium dithionite resulted in the highest ethanol production, but also 5 mM and 20 mM sodium dithionite resulted in high ethanol concentrations, about 35-40 g/L after 70 hours (see FIG. 6). Treatment with 5 mM sodium dithionite resulted in a slower effect but the fermentation reached a final ethanol concentration that was similar to the concentration reached using 7.5 mM. However, treatment with 2.5 mM and 30 mM dithionite resulted in lower final ethanol concentrations, about 30 g/L after 70 hours using 30 mM dithionite and about 10 g/L after 70 hours using 2.5 mM dithionite.

Figure 7:
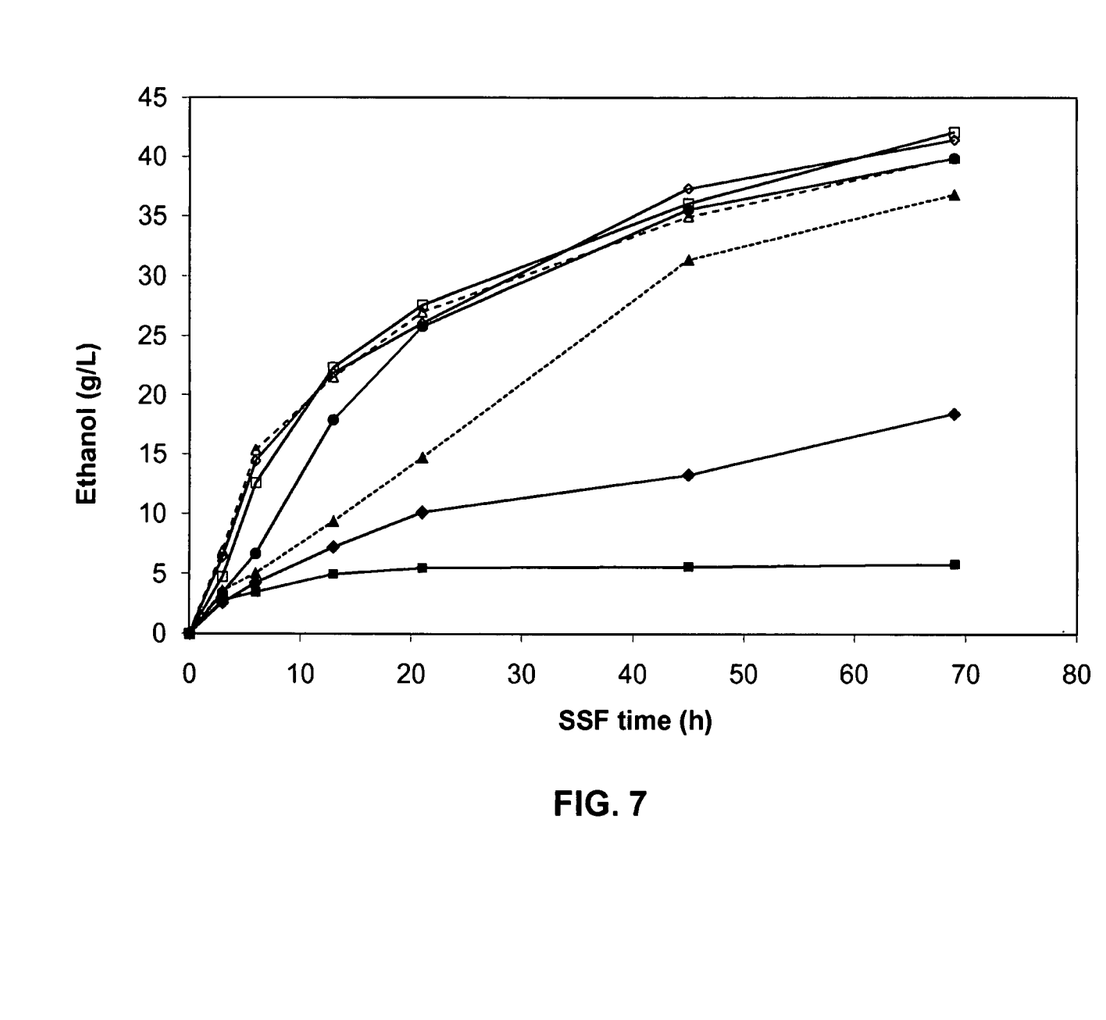
FIG. 7 shows the ethanol production during simultaneous saccharification and fermentation of spruce slurry with addition of different concentrations of sulphite. The data represent: ■: solid line: sulphite treatment (2.5 mM); ♦, solid line: sulphite treatment (5 mM); ▲, dashed line: sulphite treatment (7.5 mM); ●, solid line: sulphite treatment (10 mM); □, solid line: sulphite treatment (15 mM); ◊, solid line: sulphite treatment (20 mM); Δ, dashed line: sulphite treatment (30 mM).

Further, it was seen that treatment with 15 mM, 20 mM and 30 mM sulphite resulted in high ethanol concentrations, about 40 g/L after 70 hours (FIG. 7). Treatment with 7.5 mM and 10 mM sulphite gave a slower effect but resulted in a high final ethanol concentration, about 35-40 g/L. However, treatment with 2.5 mM and 5 mM sulphite did not result in as high final ethanol concentrations compared to treatment with sulphite concentrations above 10 mM.

Consequently, Example 3 shows that a higher ethanol concentration is obtained during fermentation if dithionite is added to a final concentration of 7.5-20 mM compared to if dithionite is added to final concentrations that are outside this range. Further, Example 3 shows that a sulphite addition of above 10 mM is more advantageous, i.e. leading to higher ethanol concentrations during fermentation, compared to if sulphite is added to a final concentration of below 10 mM.

Example 4

Detoxification of Spruce Slurry in a Simultaneous Saccharification and Fermentation (SSF) Process: Ethanol Yield Vs. Time of Addition of Sulphite or Dithionite Materials and Methods A spruce slurry was prepared as described in Example 1 above. Fermentation experiments with the yeast *Saccharomyces cerevisiae* were carried out as in the previously described Examples, except that the addition of reducing agent 10 min prior to inoculum was compared with simultaneous addition of reducing agent and inoculum, and addition of reducing agent 45, 105, 240, or 480 min after inoculum. Both sodium dithionite and sodium sulphite were included in the experiments and both were added to 10 mM. The ethanol concentration was determined after 24 hours according to the analysis described in Example 1 above.

Results

Figure 8:
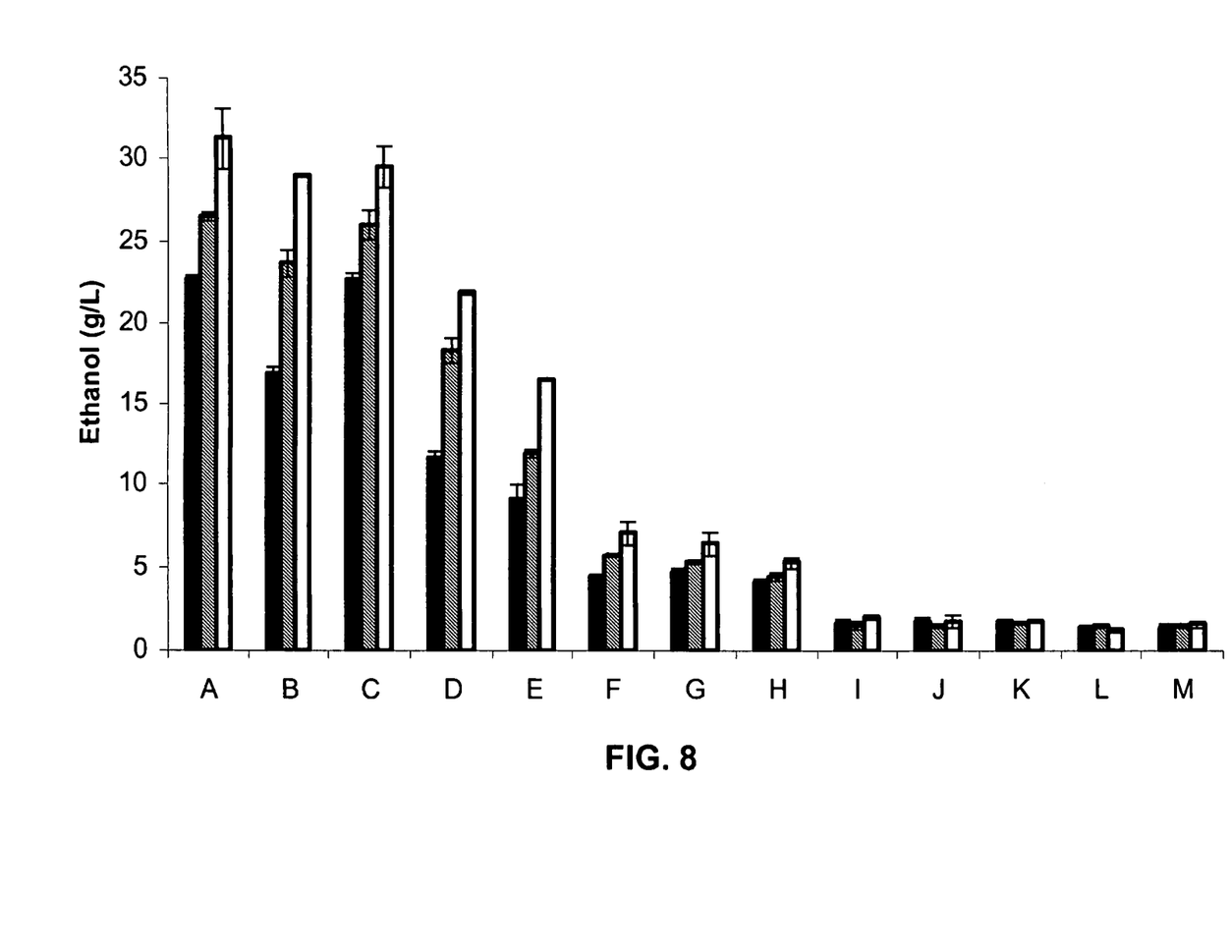

The results of the experiments of adding the reducing agents prior to inoculum, adding reducing agents simultaneous with inoculum and adding reducing agents after inoculum are shown in FIG. 8. The results clearly shows that there is no need to add the reducing agent before the fermentation is initiated, since addition after inoculum also resulted in a higher ethanol yield compared to the untreated slurry. Furthermore, addition 45 or 105 min after inoculation also resulted in improved fermentability, while addition after 240 or 480 min had minor positive effects. It was seen that the addition of dithionite resulted in better improvement than the addition of sulphite (FIG. 8).

Consequently, Example 4 demonstrates that a fermentation in which the ethanol production is inhibited may be "rescued" after the fermentation reaction has been initiated by the addition of a reducing agent. However, it appears that addition of a reducing agent before or simultaneous as the fermentation is initiated results in a higher ethanol yield. Also, it should be noted that the specific times used in this lab-scale experiment does not necessarily correspond to an industrial context. Thus additions of reducing agent more than 4 hours after the yeast addition may be efficient in a large scale fermentation.

Example 5

Detoxification of Sugarcane Bagass Slurry in a Simultaneous Saccharification and Fermentation (SSF) Process: Ethanol Yield as a Function of Dithionite and Sulphite Concentrations Materials and Methods SSF experiments were also performed with sugarcane bagass slurries. The sugarcane bagass slurries were prepared as described in Example 1. Reducing agents, dithionite and sulphite, respectively, were added 10 min prior to inoculum in concentrations of studied 7.5 and 10 mM. The ethanol concentration was measured after 13 and 45 hours according to the protocol described in Example 1.

Results

Figure 9:
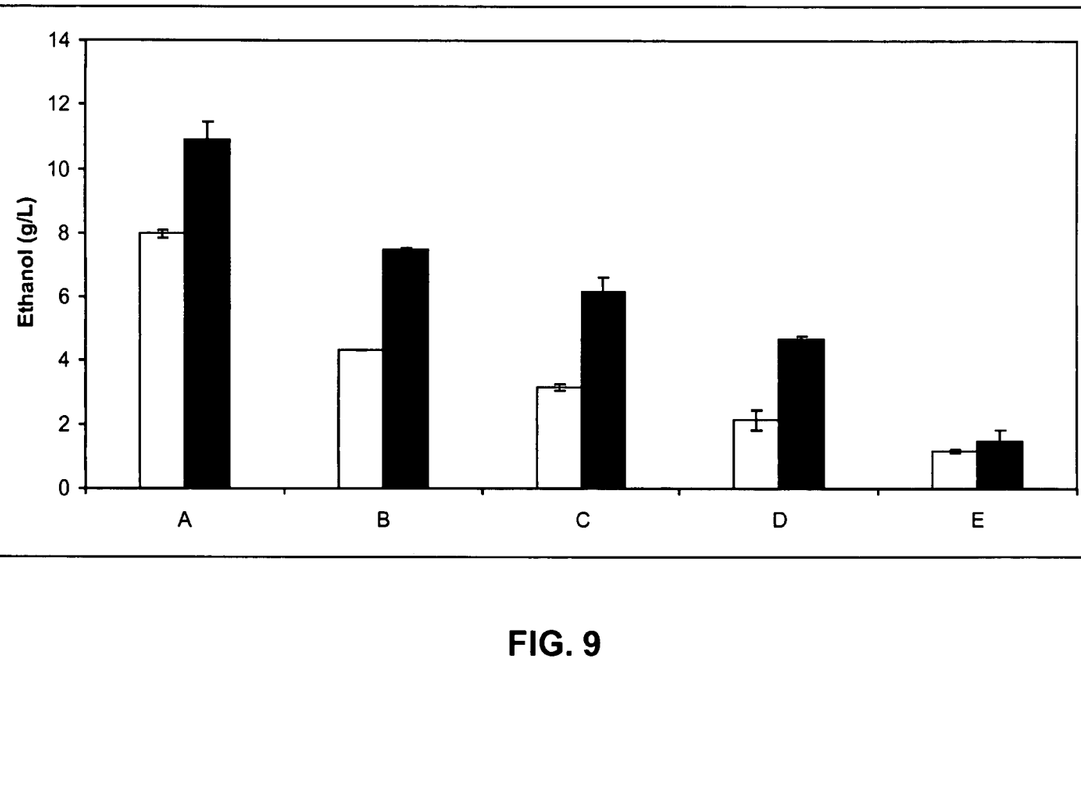
FIG. 9 shows ethanol production (g/L) after 13 (white bars) and 45 (black bars) hours of simultaneous saccharification and fermentation of sugarcane bagass slurry. The data indicate: (A) addition of 10 mM dithionite, (B) addition of 7.5 mM dithionite, (C) addition of 10 mM sulphite, (D) addition of 7.5 mM sulphite, (E) sugarcane bagass slurry with no reducing agent added. Every bar represents the mean value of two parallel SSF experiments. Error bars indicate the standard deviations.

The results of the addition of reducing agents to SSF of sugarcane bagass slurries are shown in FIG. 9. Both dithionite and sulphite resulted in improved fermentability. Both concentrations of dithionite (10 and 7.5 mM) were better than any of the sulphite concentrations (FIG. 9). Further, it was observed that addition of sulphite or dithionite did not lead to any formation of precipitates. Example 5 thus demonstrates that addition of dithionite results in higher yields of ethanol during fermentation of a sugarcane bagass slurry compared to addition of sulphite, even after 45 hours of fermentation.

The invention claimed is:

1. A method for decreasing the fermentation inhibition in a process for producing a target chemical from a pretreated lignocellulosic material, said process comprising enzymatically hydrolysing cellulose of the pretreated lignocellulosic material and fermenting the hydrolysed material,
wherein the fermentation inhibitory properties of the material subjected to fermentation is decreased by an addition of at least one reducing agent to said pretreated material or hydrolysed material, wherein said enzymatic hydrolysis and fermentation are performed simultaneously in a fermentor.

2. The method according to claim 1, wherein said at least one reducing agent is added at a temperature of 20-80° C.

3. The method according to claim 1, wherein said at least one reducing agent is added at a pH of 3-8.

4. The method according to claim 1, wherein at least one reducing agent comprises sulphur.

5. The method according to claim 4, wherein at least one reducing agent is selected from dithionite and sulphite.

6. The method according to claim 5, wherein said reducing agent is dithionite and said dithionite is added in an amount such that the concentration of dithionite during fermentation is 1-30 mM.

7. The method according to claim 5, wherein said reducing agent is dithionite and said dithionite is added in an amount such that the concentration of dithionite during fermentation is 5-25 mM.

8. The method according to claim 5, wherein said reducing agent is dithionite and said dithionite is added in an amount such that the concentration of dithionite during fermentation is 7.5-20 mM.

9. The method according to claim 1, wherein the target chemical is ethanol.

10. The method according to claim 1, wherein the material to which the reducing agent is added has a suspended solids content of at least 5% (w/w).

11. The method according to claim 1, wherein the material to which the reducing agent is added has a sugar concentration of at least 45 g/l.

12. The method according to claim 1, further comprising measuring the fermentability of said fermentation of hydrolysed material; and if said measured fermentability is below a reference value, adding the at least one reducing agent to said fermentation.

13. The method according to claim 1, further comprising recirculating process water obtained after said production of said target chemical to any step in the production of said target chemical.

14. The method according to claim 1, wherein said at least one reducing agent is added to said fermenter.

15. The method according to claim 1, wherein said at least one reducing agent is added at a temperature of 28-38° C.

16. The method according to claim 1, wherein said at least one reducing agent is added at a pH of 4-6.

17. The method according to claim 1, wherein the material to which the reducing agent is added has a suspended solids content of at least 10% (w/w).

18. The method according to claim 1, wherein the material to which the reducing agent is added has a suspended solids content of at least 12% (w/w).

19. The method according to claim 1, wherein the material to which the reducing agent is added has a sugar concentration of at least 65 g/l.

20. The method according to claim 1, wherein the material to which the reducing agent is added has a sugar concentration of at least 85 g/l.

* * * * *